(12) United States Patent
Patton

(10) Patent No.: US 7,456,150 B1
(45) Date of Patent: Nov. 25, 2008

(54) PULMONARY DELIVERY OF ACTIVE FRAGMENTS OF PARATHYROID HORMONE

(75) Inventor: John S. Patton, San Carlos, CA (US)

(73) Assignee: Mektar Therapeutics, San Carlos, CA (US)

( * ) Notice: Subject to any disclaimer, the term of this patent is extended or adjusted under 35 U.S.C. 154(b) by 0 days.

(21) Appl. No.: 09/577,264

(22) Filed: May 22, 2000

Related U.S. Application Data

(60) Continuation of application No. 09/128,401, filed on Aug. 3, 1998, now Pat. No. 6,080,721, which is a division of application No. 08/625,586, filed on Mar. 28, 1996, now Pat. No. 5,814,607, which is a continuation of application No. 08/232,849, filed on Apr. 25, 1994, now Pat. No. 5,607,915, which is a continuation of application No. 07/953,397, filed on Sep. 29, 1992, now abandoned.

(51) Int. Cl.
*A61K 38/29* (2006.01)

(52) U.S. Cl. .................. 514/12; 530/324; 530/399; 424/45; 424/469

(58) Field of Classification Search ............ 514/12; 530/324, 399; 424/45, 469
See application file for complete search history.

(56) References Cited

U.S. PATENT DOCUMENTS

| | | | |
|---|---|---|---|
| 4,698,328 | A | 10/1987 | Neer et al. |
| 4,833,125 | A | 5/1989 | Neer et al. |
| 5,011,678 | A | 4/1991 | Wang et al. |
| 5,230,884 | A | 7/1993 | Evans et al. |
| 5,302,581 | A | 4/1994 | Sarin et al. |
| 5,458,135 | A | 10/1995 | Patton et al. |
| 5,563,122 | A | 10/1996 | Endo et al. |
| 5,578,567 | A | 11/1996 | Cardinaux et al. |

FOREIGN PATENT DOCUMENTS

GB 2248550 4/1992

OTHER PUBLICATIONS

Neer et al. (1987) Osteoporosis 53:829-835.
Hesch et al. (1988) Calcif. Tisue Int. 42:341-344.
Habener et al. (1971) Proc. Natl. Acad. Sci. USA 68:2986-2991.
Patton et al. (1992) Adv. Drug Delivery Reviews 8:179-196.
Harms et al. (1987) Int. Symp. On Osteoporisis, Aalborg, Abstr. 232:723-724.
Patton (1994) J. Controlled Release 28: 79-85.
Abstract of Japanese Patent, Document No. JP 02 000111, Date Jan. 5, 1990.
Patton, "Deep-lung delivery of proteins", Modern Drug Discovery, Sep./Oct. 1998; pp. 19-28.
Hodsman et al., "Biochemical Responses to Sequential Human Parathyroid Hormone (1-38) and Calcitonin in Osteoporotic Patients," Bone and Mineral (1990), vol. 9, p. 137-152.
Hodsman et al., "Bone Densitometric and Histomorphometric Responses to Seqential Human Parathyroid Hormone (1-38) and Salmon Calcitonin in Osteoporotic Patients," Bone and Mineral (1991), vol. 14, p. 67-83.
Beaucage et al., "Deoxynucleoside Phosphoramidites—A New Class of Key Intermediates for Deoxypolynucleotide Synthesis," Tetrahedron Letters (1981), vol. 22(2), p. 1859-1862.
Hesch et al., "First Clinical Observations with hPTH(1-38), a More Potent Human Parathyroid Hormone Peptide," Horm. Metabol. Res. (1984), vol. 16, p. 559-560.

*Primary Examiner*—David Lukton
(74) *Attorney, Agent, or Firm*—Steven J. Helmer; Michael J. Mazza

(57) ABSTRACT

Systemic delivery of parathyroid hormone to a mammalian host is accomplished by inhalation through the mouth of a dispersion of an N-terminal fragment of PTH. It has been found that such respiratory delivery of the PTH fragment provides a pulsatile concentration profile of the PTH in the host's serum. PTH fragment compositions include dry powder formulations having the PTH present in a dry bulking powder, liquid solutions or suspensions suitable for nebulization, and aerosol propellants suitable for use in a metered dose inhaler.

8 Claims, 1 Drawing Sheet

Serum profiles of PTH34 in rats following intravenous and intratracheal administration Human Parathyroid Hormone PTH 84
Pulmonary Absorption in Rats

SEQUENCE LISTING

```
<160> NUMBER OF SEQ ID NOS: 1

<210> SEQ ID NO 1
<211> LENGTH: 38
<212> TYPE: PRT
<213> ORGANISM: Homo sapiens

<400> SEQUENCE: 1

Ser Val Ser Glu Ile Gln Leu Met His Asn Leu Gly Lys His Leu Asn
 1               5                  10                  15

Ser Met Glu Arg Val Glu Trp Leu Arg Lys Lys Leu Gln Asp Val His
            20                  25                  30

Asn Phe Val Ala Leu Gly
            35
```

PULMONARY DELIVERY OF ACTIVE FRAGMENTS OF PARATHYROID HORMONE

CROSS REFERENCE TO RELATED APPLICATIONS

This application is a continuation of, and claims the benefit of priority from, application Ser. No. 09/128,401; filed on Aug. 3, 1998, now U.S. Pat. No. 6,080,721, which is a division of application Ser. No. 08/625,586; filed on Mar. 28, 1996, now U.S. Pat. No. 5,814,607, which is a continuation of application Ser. No. 08/232,849; filed on Apr. 25, 1994, now U.S. Pat. No. 5,607,915, which is a continuation of application Ser. No. 07/953,397; filed on Sep. 29, 1992, now abandoned, the full disclosures of which are incorporated herein by reference.

BACKGROUND OF THE INVENTION

1. Field of the Invention

The present invention relates generally to methods and compositions for systemic administration of parathyroid hormone to mammalian hosts. More particularly, the present invention relates to pulmonary administration of active parathyroid hormone fragments to provide pulsatile serum concentration profiles.

Human parathyroid hormone (PTH) is an 84 amino acid protein that is involved in calcium and phosphorus homeostasis and control of bone growth and density. N-terminal fragments of PTH, particularly those consisting of amino acids 1-34 and 1-38, retain the full biological activity of the intact protein. Recently, the use of PTH and PTH fragments in combination with vitamin D or dietary calcium was found to be effective in the treatment of osteoporosis when administered to a host on a periodic, preferably daily, basis.

Heretofore, the administration of PTH and PTH fragments has generally been accomplished subcutaneously, i.e., through injection. The need to inject PTH (or any other drug) on a daily basis, however, is undesirable. Most patients have an aversion to self-injection of drugs, and the need to visit a clinic or doctor's office for administration is inconvenient and burdensome. While other forms of administration have been suggested, such as oral delivery to the stomach, transdermal delivery, and nasopharyngeal absorption, none of these delivery routes has been proven to be effective and each suffers from certain drawbacks. Oral delivery results in very low bioavailability of polypeptide drugs, usually below 1%, due to degradation in the gastrointestinal tract. Moreover, the epithelial lining of the gastrointestinal tract is impermeable to most polypeptides. Nasopharyngeal and transdermal delivery avoid the problems of enzyme degradation, but usually require penetration enhancers in order to effect systemic absorption. Even with such penetration enhancers, bioavailability will usually be very low, and the penetration enhancers can often cause undesirable irritation. In the case of nasopharyngeal administration, penetration enhancers can often damage the nasal epithelium and chronic use has been associated with hyperplasia of the nasal lining.

Pulmonary or respiratory delivery of polypeptide drugs has also been suggested. Relatively large proteins, such as growth factors and cytokines which are typically larger than 150 amino acids, are often readily absorbed through the cellular lining of the alveolar region of the mammalian lung. Advantageously, such absorption can be achieved without the use of penetration enhancers. The pulmonary absorption of smaller proteins, usually below 100 amino acids in length, is much less predictable. Many smaller native polypeptides are not absorbed by the mammalian lung, but certain examples such as insulin (51 amino acids) and calcitonin (32 amino acids) have been found to be systemically absorbed when delivered to the lung. Even when a protein drug is systemically absorbed by a host through the lung, the pharmacological kinetics of the drug are unpredictable. Thus, both the amount and timing of drug bioavailability are unpredictable.

It is presently believed that PTH is most effectively delivered to a patient in a pulsatile fashion. That is, serum concentrations of PTH should rise rapidly after administration and fall rapidly after a peak has been reached, generally resulting in a spike in the serum concentration profile. Thus, it is advantageous for any route of PTH delivery to provide such a serum concentration profile.

For these reasons, it would be desirable to provide alternative delivery methods for parathyroid hormone which are patient acceptable. Such methods should avoid subcutaneous injection, limit irritation to the skin and body mucosa, and provide a desired pulsatile delivery profile discussed above. Such methods should further provide for high levels of PTH bioavailability, be amenable to self-administration by the patient, and be economic.

2. Description of the Background Art

U.S. Pat. Nos. 4,833,125 and 4,698,328, describe the administration of active parathyroid hormone fragments in combination with vitamin D or a dietary calcium supplement. Suggested administration routes include parenteral by injection, rapid infusion, nasopharyngeal absorption, dermal absorption, or oral. See also, Neer et al. (1987) Osteoporosis 53:829-835. U.S. Pat. No. 5,011,678, describes the use of amphophilic steroids as a penetration enhancer for nasal or bronchopulmonary delivery of proteins and polypeptides, listing parathyroid hormone as one of a "veritable host" of proteins which could be delivered with the enhancer. Parathyroid hormone (full length) is secreted naturally from the parathyroid gland as a series of spikes in a pulsatile fashion which is analogous to pituitary hormones (Harms et al. (1987) Int. Symp. on Osteoporosis, Aalborg, Abstract 232). The full length hormone is rapidly broken down in the circulation to several fragments which are the dominant serum forms. It is hypothesized that an intermittent or pulsatile secretion pattern for parathyroid hormone is necessary to maintain its bone restoring properties (Hesch et al. (1988) Calcif. Tissue Int. 42:341-344 and Habener et al. (1971) Proc. Natl. Acad. Sci. USA 68:2986-2991). Patton and Platz (1992) Adv. Drug Deliver. Rev. 8:179-196. describe methods for delivering proteins and polypeptides by inhalation through the deep lung.

SUMMARY OF THE INVENTION

According to the present invention, methods and compositions for the systemic delivery of parathyroid hormone (PTH) to a mammalian host, particularly a human patient suffering from or at risk of osteoporosis, provide for a preferred pulsatile concentration profile of the PTH in the host's serum after administration. In particular, the methods of the present invention rely on pulmonary or respiratory delivery of a biologically active N-terminal fragment of PTH, where delivery of the fragment through the alveolar region of the lung results in a rapid concentration spike of PTH in the host serum followed by a quick decrease in concentration. Surprisingly, pulmonary delivery of intact PTH protein under the same conditions will result in a relatively constant serum concentration of PTH over an extended time period. The ability to obtain the desired pulsatile serum concentration profile by pulmonary delivery of the PTH fragments, in contrast to the delivery of intact PTH, could not have been predicted with any degree of certainty prior to the work reported herein.

According to an exemplary embodiment, the method of the present invention comprises dispersing a preselected amount of the PTH fragment in a volume of gas to produce an aerosolized bolus. The PTH fragment usually consists of the N-terminal 34 or 38 amino acids of the PTH molecule (but may be an N-terminal fragment of any size which displays the desired pharmacokinetic profile, usually being 50 or fewer amino acids), and the dispersion may be produced by introducing a dry powder of the fragment into a high velocity gas stream, by nebulizing a liquid solution or suspension of the fragment, or by releasing a propellant containing the PTH fragment through a nozzle. The patient then inhales the aerosolized bolus through the mouth and into the alveolar region of the lungs. By repeating the dispersing and inhaling steps a sufficient number of times, a desired total dosage of the PTH fragment can be delivered to the patient.

Pharmaceutical compositions according to the present invention include dry powder formulations where the PTH fragment is present as a powder having a mean particle size in the range from 0.5 µm to 5 µm in a pharmaceutically acceptable dry bulking powder, where the PTH is present at from 1% to 10%. A pharmaceutical composition suitable for nebulization comprises the biologically active fragment of PTH present in an aqueous buffer at pH 4-6 in a concentration in the range from 1 mg/ml to 20 mg/ml. Pharmaceutical compositions suitable for propellant dispersion comprise a powder of the PTH having a mean particle size in the range from 0.5 µm to 5 µm present in an aerosol propellant.

In addition to the preferred pulsatile pharmacokinetic serum profile of the PTH fragments, the methods and compositions of the present invention provide a high level of patient acceptability. PTH administration does not require injection and can be self-administered by the patient on a daily basis, usually without complications such as those associated with transdermal and intranasal delivery. The methods and compositions of the present invention also provide for a high level bioavailability of the PTH, and are economic.

DESCRIPTION OF SPECIFIC EMBODIMENTS

Figure 1:
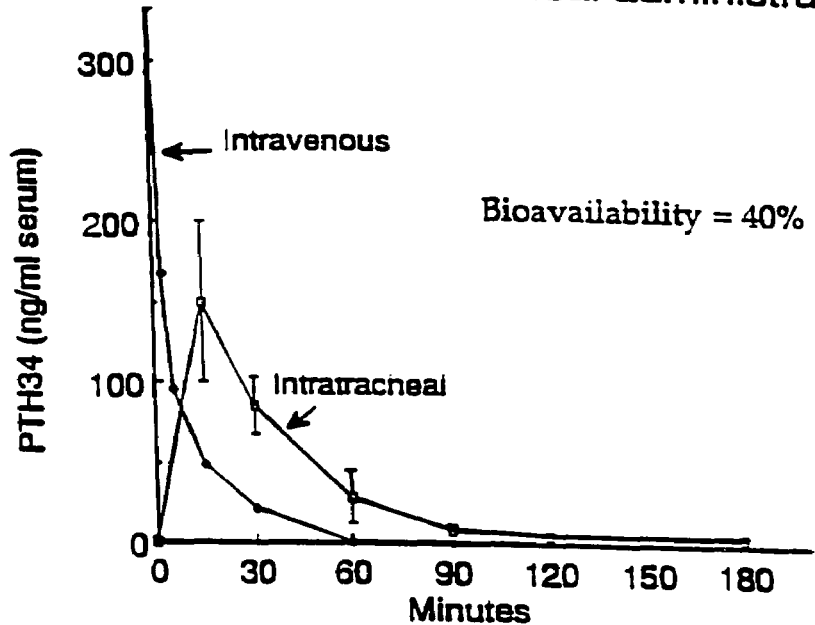
FIG. 1 is a graph illustrating the serum profile over time of PTH34 administered intravenously and intratracheally to rats, as described in detail in the Experimental section hereinafter.

Parathyroid hormone (PTH) is delivered to a mammalian host by inhalation into the alveolar region of the host's lungs. The cellular lining of the deep mammalian lung is extremely thin (0.1 µm) and has been found to be naturally permeable to both full length PTH and certain biologically active and N-terminal fragments of PTH, as described below. Surprisingly, however, such pulmonary or respiratory delivery of the PTH fragments only (and not the full length PTH) has been found to provide a desired pulsatile serum concentration profile of the PTH, as is believed to enhance the biological activity of the PTH, particularly when treating osteoporosis.

Thus, the present invention provides for the pulmonary or respiratory delivery of biologically active N-terminal fragments of PTH by inhalation by a patient through the mouth, where such fragments have a size which is less than that of full size native human PTH (human PTH is 84 amino acids) and which results in a pulsatile serum concentration profile characterized by a rapid rise to a peak and followed by a rapid fall. The PTH fragments will preferably be fragments of human PTH (or recombinantly produced polypeptides having the sequence of human PTH), typically including up to about 50 amino acids from the N-terminus of the PTH molecule, more preferably consisting of either amino acids 1-34 or amino acids 1-38 of human PTH, as set forth in Table 1 below.

Useful biologically active fragments of PTH also include chemically modified parathyroid hormone fragments which retain the activity associated with parathyroid hormone. The necessary activity is the stimulation of bone formation. Modifications that may be considered include:

(1) PTH fragments with carboxyl amino acid extensions beyond position 34 (but usually not beyond position 50) of the human PTH molecule, or aminoterminal extensions, or amino acid substitutions that produce other desirable features, such as an alpha-carboxyl amide at the carboxyl terminus. A desirable modification would enhance activity in vivo.

(2) PTH fragments extended to include amino acids 1-38, which would enhance receptor binding and hence the activity per mole.

(3) PTH fragments chemically modified so as to enhance through absorption through the alveolar region of the lung.

(4) Physiologically acceptable salts and esters of PTH fragments.

A PTH fragment obtainable from a mammal is generally preferred over other types of parathyroid hormone fragments, such as derivatives. Use of a PTH fragment consisting of the first thirty-four amino acid residues of human parathyroid hormone (hereafter abbreviated "PTH34") is especially preferred for use in humans. Other preferred PTH fragments are those which display some or all of the following desirable features: increased potency with regard to the necessary activity, increased ease of administration, increased selectivity to decrease potential side effects, and decreased antigenicity in humans to avoid an adverse immune response. PTH fragments molecules having the sequences 1-34 or 1-38 of Table 1 are Particularly preferred:

TABLE 1

(SEQ ID NO: 1)

| 1 | | | | 5 | | | | |
|---|---|---|---|---|---|---|---|---|
| $H_2N$-Ser-Val-Ser-Glu-Ile-Gln-Leu-Met-His- | | | | | | | | |
| 10 | | | | 15 | | | | |
| Asn-Leu-Gly-Lys-His-Leu-Asn-Ser-Met-Glu- | | | | | | | | |
| 20 | | | | 25 | | | | |
| Arg-Val-Glu-Trp-Leu-Arg-Lys-Lys-Leu-Gln- | | | | | | | | |
| 30 | | | | 35 | | | | |
| Asp-Val-His-Asn-Phe-Val-Ala-Leu-Gly-COOH | | | | | | | | |

The preferred PTH34 and PTH38 fragments may be obtained commercially from suppliers such as Peninsula Laboratories, Inc., Belmont, Calif.; Sigma Chemical Co., St. Louis, Mo.; Bachem Calif., Torrance, Calif.; and others. Alternatively, the PTH fragments may be produced recombinantly by expression in cultured cells of recombinant DNA molecules encoding the desired fragment of the PTH molecule. Suitable recombinant expression systems and methods are well described in the literature. See, for example, Manniatis, *Molecular Cloning: A Laboratory Manual*, Cold Spring Harbor, N.Y., 1982. The DNA molecules which are expressed may themselves be synthetic or derived from a natural source. Synthetic polynucleotides may be synthesized by well-known techniques, for example, single-stranded DNA fragments may be prepared by the phosphoraminite method first described by Beaucage and Carruthers (1981) Tett. Lett. 22:1859-1862. A double-stranded fragment may then be obtained either by synthesizing the complementary strand and annealing the strands together under appropriate conditions, or by adding the complementary strand using DNA polymerase with an appropriate primer sequence. The preparation of synthetic DNA sequences is conveniently accomplished using automated equipment available from suppliers, such as Applied Biosystems, Inc., Foster City, Calif.

The PTH fragments will be formulated in pharmaceutically acceptable compositions suitable for pulmonary or respiratory delivery to a mammalian host, usually a human host at risk of or suffering from osteoporosis. Particular formulations include dry powders, liquid solutions or suspensions suitable for nebulization, and propellant formulations suitable for use in metered dose inhalers (MDI's). The preparation of such formulations is well described in the patent, scientific, and medical literatures, and the following descriptions are intended to be exemplary only.

Dry powder formulations will typically comprise the PTH fragment in a dry, usually lyophilized, form with a particle size within a preferred range for deposition within the alveolar region of the lung, typically from 0.5 µm to 5 µm. Respirable powders of PTH fragments within the preferred size range can be produced by a variety of conventional techniques, such as jet-milling, spray-drying, solvent precipitation, and the like. Dry powders can then be administered to the patient in conventional dry powder inhalers (DPI's) that use the patient's inspiratory breath through the device to disperse the powder or in air-assisted devices that use an external power source to disperse the powder into an aerosol cloud. A particularly useful dry powder disperser is described in copending application Ser. No. 07/910,048, assigned to the assignee of the present invention, the full disclosure of which is incorporated herein by reference.

Dry powder devices typically require a powder mass in the range from about 1 mg to 10 mg to produce a single aerosolized dose ("puff"). Since the required dose of PTH fragment will generally be much lower than this amount, as discussed below, the PTH powder will typically be combined with a pharmaceutically acceptable dry bulking powder, with the PTH present usually at from about 1% to 10% by weight. Preferred dry bulking powders include sucrose, lactose, trehalose, human serum albumin (HSA), and glycine. Other suitable dry bulking powders include cellobiose, dextrans, maltotriose, pectin, sodium citrate, sodium ascorbate, mannitol, and the like. Typically, suitable buffers and salts may be used to stabilize the PTH fragments in solution prior to particle formation. Suitable buffers include phosphate, citrate, acetate, and tris-HCl, typically at concentrations from about 5 mM to 50 mM. Suitable salts include sodium chloride, sodium carbonate, calcium chloride, and the like. Other additives, such as chelating agents, peptidase inhibitors, and the like, which would facilitate the biological activity of the PTH fragment once it is dissolved within the lung would be appropriate. For example, ethylenediaminetetraacetic acid (ETDA) would be useful as a chelator for divalent cations which are peptidase cofactors.

Liquid formulations of PTH fragments for use in nebulizer systems can employ slightly acidic buffers (pH 4-6) with PTH concentrations of from about 1 mg/ml to 20 mg/ml. Suitable buffers include acetate, ascorbate, and citrate, at concentrations of 5 mM to 50 mM. These buffers can act as antioxidants, or other physiologically acceptable antioxidants can be added to protect free methionines in the PTH fragment against oxidation. Other components may be added to enhance or maintain chemical stability, including chelating agents, protease inhibitors, isotonic modifiers, inert gases, and the like. A preferred type of nebulizer suitable for delivering such liquid formulations is described in copending application Ser. No. 07/910,048, the disclosure of which has previously been incorporated herein by reference.

For use in MDI's, the PTH fragments of the present invention will be dissolved or suspended in a suitable aerosol propellant, such as a chlorofluorocarbon (CFC) or a hydrofluorocarbon (HFC). Suitable CFC's include trichloromonofluoromethane (propellant 11), dichlorotetrafluoroethane (propellant 114), and dichlorodifluoromethane (propellant 12). Suitable HFC's include tetrafluoroethane (HFC-134a) and heptafluoropropane (HFC-227).

Preferably, for incorporation into the aerosol propellant, the PTH fragments of the present invention will be processed into respirable particles as described for the dry powder formulations. The particles are then suspended in the propellant, typically being coated with a surfactant to enhance their dispersion. Suitable surfactants include oleic acid, sorbitan trioleate, and various long chain diglycerides and phospholipids.

Such aerosol propellant formulations may further include a lower alcohol, such as ethanol (up to 30% by weight) and other additives to maintain or enhance chemical stability and physiological acceptability.

Pulmonary or respiratory administration of PTH fragments according to the present invention will be useful in the treatment of osteoporosis, where the PTH fragment will be administered in combination with vitamin D calcitonin, and/or dietary calcium supplements. Such treatment methods are well described in U.S. Pat. Nos. 4,698,328 and 4,833,125, the disclosures of which have previously been incorporated herein by reference.

The total aerosolized dosage of PTH fragment for the treatment of osteoporosis will typically be in range from about 100 µg to 2,000 µg per day, usually being in the range from about 250 µg to 1000 µg per day. Such dosages will result in a total systemic availability (i.e., amount which is delivered to the blood) in the range from about 50 µg to 500 µg per day, usually from 100 µg to 250 µg, per day. Precise dosages will, of course, vary depending on the activity of the particular PTH fragment or analog employed, and other known pharmacokinetic factors. Usually, the total dosage of PTH fragment will be delivered in a plurality of separate aerosolized doses, typically being at least two and, often being from three to ten, where each aerosolized bolus contains from 50 µg to 500 µg of the PTH fragment.

Pulmonary delivery of PTH fragments according to the methods of the present invention has been found to provide a desired pulsatile serum concentration profile. The pulsatile serum PTH fragment concentration profile will typically peak within 30 minutes after administration, with serum concentrations falling rapidly, typically to below 50% of maximum within 30 minutes of the peak and to below 25% within 60 minutes of the peak.

In the case of a dry powder formulation, a sufficient amount of dry bulking powder will be added so that a total dosage of PTH fragment within the above range can be achieved with one or more aerosolized boluses which are to be inhaled by the patient. Typically, the active PTH fragment will be present at from about 1% to 25% by weight of the powder, with aerosolized boluses including from 1 mg to 10 mg of the powder. Liquid formulations suitable for use in nebulizers typically have a concentration of the PTH fragment in the range from about 1 mg/ml to 20 mg/ml, with the total volume of nebulized liquid needed to deliver the bolus in the range from about 0.1 ml to 1 ml. The aerosol propellant formulations will be delivered by MDI at about 0.5 mg to 5 mg of PTH fragment per aerosol dose. Because of the inefficiencies of MDI devices, only a small portion, typically in the range of 5% to 20%, of the drug will reach the lungs. Thus, a sufficient amount of the PTH fragment can be delivered in from two to five aerosolized boluses, with about 1 mg of the PTH fragment in each of the boluses.

The following examples are offered by way of illustration, not by way of limitation.

EXPERIMENTAL

Materials and Methods

Recombinant human parathyroid hormone (PTH84) was obtained from Peninsula Laboratories, Inc., Belmont, Calif. (Lot No. 800929). A recombinant fragment (amino acids 1-34) of human parathyroid hormone (PTH34) was obtained from Sigma Chemical Co., St. Louis, Mo. (Lot No. 098F48052).

Rats (approximately 300-320 g) were obtained from Simonsone Labs, Gilroy, Calif.

PTH84 and PTH34 were administered to rats intravenously (IV) and intratracheally (IT) suspended in 100 µl of 20 mM citrate buffer, pH 5. Dosages were 5 µg for IV administration of PTH84, 100 µg for IT administration of PTH84, 25 µg for IV administration of PTH34, and 100 µg for IT administration of PTH34. IT administration was performed by making a one inch incision in the medial neck region and exposing the trachea. The polypeptide suspensions were injected into the trachea using a tuberculin syringe with a 30 gauge needle over approximately one minute. The head of the rat was held upright during the intratracheal injection and for one additional minute thereafter.

Rat serum was assayed for PTH34 at periodic intervals after PTH34 administration using a Nichols Instrument INS PTH assay kit which measures PTH34 with no cross-reactivity to PTH28-54, PTH44-68, and PTH53-84. Samples were diluted as necessary to obtain measurable concentrations.

Rat serum was assayed for PTH84 with Nichols Instrument Alegro assay kit for human PTH which measures PTH84 with no cross-reactivity with PTH34, PTH39-68, PTH44-68, PTH53-84, and PTH39-84. Samples were diluted as necessary to obtain measurable concentrations.

Results

Figure 2:
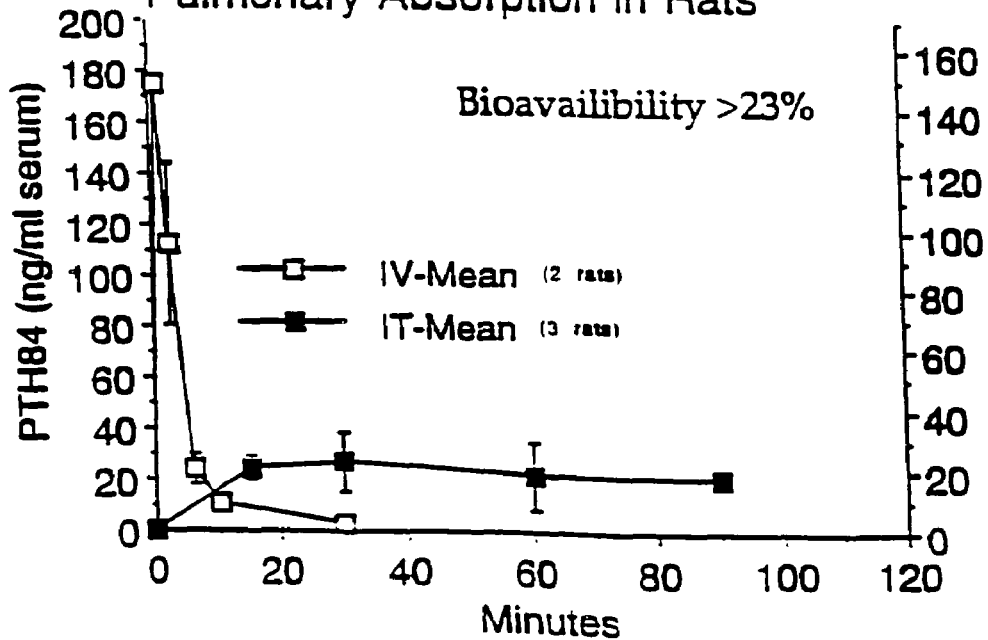
FIG. 2 is a graph illustrating the serum profile of PTH84 administered intravenously and intratracheally to rats, as described in detail in the Experimental section hereinafter.

The serum profiles of PTH34 and PTH84 in rats following IV and IT administration are shown in FIGS. 1 and 2, respectively. The absolute bioavailability of PTH34, which indicates the percentage of total administered hormone that got into the blood, was about 40%. The absorption profile of PTH34 exhibited a spike at 15 minutes with activity diminishing rapidly thereafter. This is similar to the profile seen after subcutaneous injection. In contract, PTH84 at the same intratracheal dose, exhibited a very different absorption profile. Instead of a spike, a plateau in serum levels occurred that did not diminish significantly during the 90 minutes of the experiment. The bioavailability of PTH84 at 90 minutes was about 23% (as measured by the truncated area under the curve up to 90 minutes), but the slow sustained release absorption profile suggests that serum levels would have persisted for longer times.

Although the foregoing invention has been described in detail for purposes of clarity of understanding, it will be obvious that certain modifications may be practiced within the scope of the appended claims.

---

---

What is claimed is:

1. A method for treating osteoporosis in a mammalian host comprising, dispersing a powder pharmaceutical composition consisting essentially of a therapeutically effective amount of a biologically active N-terminal fragment of parathyroid hormone, a pharmaceutically acceptable bulking agent and optionally, an aerosol propellant in a volume of gas to produce an aerosolized bolus; and administering by inhalation to said host's alveolar region said aerosolized bolus, wherein at least two boluses are administered, and wherein said administration results in a pulsatile serum concentration having a peak concentration within about 30 minutes after administration, followed within about 30 minutes by a decrease to below about 50% of said peak.

2. The method of claim 1, wherein the mammalian host is human.

3. The method of claim 1, wherein the aerosol propellant, if present, comprises a chlorofluorocarbon or a hydrofluorocarbon.

4. The method of claim 1, wherein the aerosol propellant comprises a hydrofluorocarbon.

5. The method of claim 4, wherein the hydrofluorocarbon comprises at least one member selected from tetrafluoroethane and heptafluoropropane.

6. The method of claim 1, wherein the powder comprises a mean particle size in the range from 0.5 μm to 5 μm.

7. A method for treating osteoporosis in a mammalian host comprising administering by inhalation an aerosolized bolus of a pharmaceutical composition consisting essentially of a therapeutically effective amount of a biologically active N-terminal fragment of parathyroid hormone, a pharmaceutically acceptable bulking agent and an aerosol propellant, wherein the bulking agent comprises at least one member selected from sucrose, lactose, trehalose, human serum albumin, glycine, cellobiose, dextrans, maltotriose, pectin, sodium citrate, sodium ascorbate, and mannitol, and wherein said administration results in a pulsatile serum concentration having a peak concentration within about 30 minutes after administration, followed, within about 30 minutes by a decrease to below about 50% of said peak.

8. The method of claim 1, wherein the biologically active N-terminal fragment of parathyroid hormone is PTH34.

* * * * *